United States Patent
Zhang et al.

(10) Patent No.: US 8,859,565 B2
(45) Date of Patent: Oct. 14, 2014

(54) COMPOUND FOR INHIBITING TYPE 5 PHOSPHODIESTERASE AND PREPARATION METHOD THEREOF

(76) Inventors: Nan Zhang, Nanjing (CN); Rong Zhong, Nanjing (CN)

( * ) Notice: Subject to any disclaimer, the term of this patent is extended or adjusted under 35 U.S.C. 154(b) by 0 days.

(21) Appl. No.: 13/512,524

(22) PCT Filed: Jul. 30, 2010

(86) PCT No.: PCT/CN2010/075587
§ 371 (c)(1),
(2), (4) Date: Aug. 9, 2012

(87) PCT Pub. No.: WO2012/000212
PCT Pub. Date: Jan. 5, 2012

(65) Prior Publication Data
US 2013/0116265 A1    May 9, 2013

(30) Foreign Application Priority Data
Jul. 2, 2010    (CN) .......................... 2010 1 0221658

(51) Int. Cl.
| | | |
|---|---|---|
| *A01N 43/90* | (2006.01) | |
| *A61K 31/519* | (2006.01) | |
| *C07D 487/00* | (2006.01) | |
| *C07D 487/04* | (2006.01) | |
| *C07C 59/265* | (2006.01) | |

(52) U.S. Cl.
CPC ............ *C07D 487/04* (2013.01); *C07C 59/265* (2013.01); *A61K 31/519* (2013.01)
USPC ........................................ 514/262.1; 544/262

(58) Field of Classification Search
None
See application file for complete search history.

(56) References Cited

FOREIGN PATENT DOCUMENTS

CN        1517349    *    8/2004    ........... C07D 487/04

* cited by examiner

*Primary Examiner* — Jeffrey H Murray
(74) *Attorney, Agent, or Firm* — Pauly, Devries Smith & Deffner, LLC

(57) ABSTRACT

The present invention discloses a compound of formula (I) and citrate thereof as type 5 phosphodiesterase inhibitor, a preparation method thereof, and a pharmaceutical composition including the compound of formula (I) and citrate thereof. The experimental results of the present invention prove that the compound of formula (I) and citrate thereof can inhibit activity of type 5 phosphodiesterase, and can be used for treating erectile dysfunction, inhibiting platelet aggregation and treating thrombosis, decreasing pulmonary hypertension and treating cardiovascular diseases, treating asthma and treating diabetes gastroparesis.

4 Claims, No Drawings

COMPOUND FOR INHIBITING TYPE 5 PHOSPHODIESTERASE AND PREPARATION METHOD THEREOF

CROSS-REFERENCE TO RELATED APPLICATIONS

This application is a national stage application under 35 U.S.C. 371 of International Patent Application Serial No. PCT/CN2010/075587, entitled "COMPOUND FOR INHIBITING TYPE 5 PHOSPHODIESTERASE AND PREPARATION METHOD THEREOF," filed Jul. 30, 2010, which claims priority from Chinese Patent Application No. 201010221658.7, filed Jul. 2, 2010, the disclosures of which are incorporated by reference in their entirety.

FIELD OF INVENTION

This invention relates to a compound for inhibiting type 5 phosphodiesterase, its salts, its preparation methods and pharmaceutical compositions containing the compound or its salts.

BACKGROUND

Cyclic adenosine monophosphate (cAMP) and cyclic guanosine monophosphate (cGMP) are important second messengers in cell, and the level of cAMP and cGMP in cell is important to regulate various functions of the cell. Enzymes participated in regulating cAMP and cGMP level in cell include adenylate cyclase (AC), guanylate cyclase (GC) and phosphodiesterase (PDE). Balance coordination of these enzymes maintains the level of cAMP and cGMP in cell within normal ranges. In some disease states (e.g., hypertension, angina pectoris, etc.), it is found that the level of cAMP and cGMP in cell drops. To increase the level of cAMP and cGMP in cell, two options can be implemented: 1) to activate AC and GC, and 2) to inhibit PDE, in which the second option has better effects. In recent years, there is a great passion to study and develop PDE inhibitor, and clinical application of isoenzyme-selective PDE inhibitor has achieved breakthrough progress. Currently, the experimental results of cDNA molecule clone have proved that there are at least 10 kinds of PDE gene families in mammals. For each PDE gene family, there are a plurality of PDE isoenzyme subtypes due to splice variant, in which type 5 phosphodiesterase (PDE5) family can selectively hydrolyze cGMP, and is widely distributed in individual body organs.

PDE5 Inhibitor has the Following Pharmacological Functions and Clinical Applications:

(1) Inhibiting platelet aggregation and anti-thrombosis: ideal antithrombotic drugs shall inhibit platelet aggregation without relaxation of vascular smooth muscle, to avoid causing the ischemia site to become further ischemia. Both PDE3 and PDE5 inhibitors have the function of inhibiting platelet aggregation. However, in view that PDE5 inhibitor has reduced relaxation of vascular smooth muscle, it has substantial advantage in treating arterial thrombotic diseases. The typical PDE5 inhibitor—dipyriamole has good antithrombotic effects.

(2) Decreasing pulmonary hypertension and anti-cardiovascular diseases: abnormality of pulmonary vascular resistance often is an important factor to cause cardiovascular diseases. In animal model experiments, selective PDE5 inhibitor—zaprinast can substantially increase the effective time and intensity of nitric oxide, and has relatively strong effects to lower pulmonary hypertension. Clinically it is used to treat angina pectoris, hypertension and myocardial infarction. In the latest report, PDE5 inhibitor—E-4010 can increase the survival rate of rats having hypertension induced by monocrotaline.

(3) Anti-asthma: It is reported that experiments using pigs as animal model show that PDE5 inhibitor—SR-265579 has therapeutic effects to bronchiectasis induced by histamine;

(4) Treating diabetes gastroparesis: It is reported that to rats having diabetes, PDE5 inhibitor—sildenafil citrate can reverse delayed gastric emptying, and has certain therapeutic and improving effects to digestive system autonomic neuropathy complicated by diabetes.

(5) Treating erectile dysfunction: Since PDE5 is widely distributed in cavernous body of penis, PDE5 inhibitor can cause cGMP level in the cavernous body of penis to rise. Upon a series of physiological and biochemical reactions, the vascular smooth muscle is relaxed, and the penis erects. Unlike prostaglandin E1, PDE5 inhibitor will not cause pathologic erection, its function still needs sexual stimulus.

SUMMARY

In view of the above pharmacological functions of PDE5 inhibitor, we modify chemical structure of sildenafil with chemical molecular modification method to produce new compounds and their citrate, i.e., 5-[2-ethoxyphenyl-5-(3,4,5-trimethyl piperazinyl)-sulfonyl]-1-methyl-3-propyl-1,6-dihydro-7H-pyrazolo[4,3-d]pyrimidine-7-ketone and citrate (ZTH) thereof. It is found that ZTH can effectively inhibit activity of PDE5 enzyme. This is how this invention comes. The first object of the present invention is to provide a new compound that can inhibit activity of type 5 phosphodiesterase and its salt such as citrate. The second object of the present invention is to provide a method for preparing the new compound and its citrate. The third object of the present invention is to provide a pharmaceutical composition that contains the new compound or its salt such as citrate.

The present invention provides a compound represented by formula I, and its pharmaceutical citrate represented by formula II:

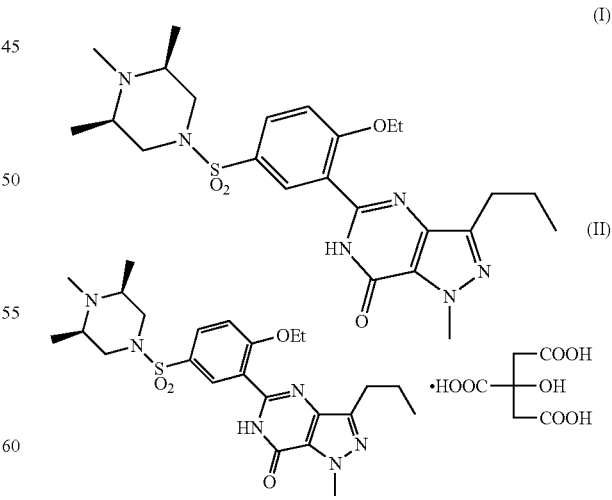

The chemical name of the compound represented by formula I is: 5-[2-ethoxyphenyl-5-(3,4,5-trimethyl piperazinyl)-sulfonyl]-1-methyl-3-propyl-1,6-dihydro-7H-pyrazolo[4,3-d]pyrimidine-7-ketone. Nuclear magnetic resonance technology is used to illustrate its structure and mass spectrum computates molecular weight:

$^1$H-NMR (400 MHz, MeOD) δ8.180-8.185 (d, J=2 Hz, 1H), 7.880-7.908 (dd, $J_1$=2.4 Hz, $J_2$=8.8 Hz, 1H), 7.356-7.379 (d, J=9.2 Hz, 1H), 4.284-4.337 (q, J=14 Hz, 2H), 4.234 (s, 3H), 3.575-3.603 (d, J=11.2 Hz, 2H), 2.865-2.902 (t, J=7.2 Hz, 2H), 2.377 (br, 2H), 2.261 (s, 3H), 2.112-2.168 (t, J=11.2 Hz, 2H), 1.795-1.851 (m, 2H), 1.465-1.500 (t, J=7.2 Hz, 3H), 1.090-1.105 (d, J=6 Hz, 6H), 0.978-1.015 (t, J=7.2 Hz, 3H). MS 503 [M+H]$^+$

The citrate of formula II is obtained from reaction of the compound by formula I and citric acid. The chemical name of the citrate represented by formula II is: 5-[2-ethoxyphenyl-5-(3,4,5-trimethyl piperazinyl)-sulfonyl]-1-methyl-3-propyl-1,6-dihydro-7H-pyrazolo[4,3-d]pyrimidine-7-ketone citrate. Analysis is made with nuclear magnetic resonance: $^1$H-NMR (400 MHz, CDCl$_3$) δ8.164-8.170 (d, J=2.4 Hz, 1H), 7.914-7.942 (dd, $J_1$=2.4 Hz, J2=8.8 Hz, 1H), 7.363-7.385 (d, J=8.8 Hz, 1H), 4.276-4.329 (q, J=14 Hz, 2H), 4.231 (s, 3H), 3.746-3.776 (d, J=11.2 Hz, 2H), 2.986 (br, 2H), 2.858-2.895 (t, J=7.2 Hz, 2H), 2.792 (s, 2H), 2.739 (s, 2H), 2.590 (s, 3H), 2.406-2.464 (t, J=11.6 Hz, 2H), 1.784-1.839 (m, 2H), 1.448-1.483 (t, J=7.2 Hz, 3H), 1.253-1.269 (d, J=6.4 Hz, 6H), 0.972-1.009 (t, J=7.2 Hz, 3H).

The compound of formula I is obtained mainly with cis-2,6-lupetazin and 5-(2-ethoxyphenyl)-1-methyl-3-propyl-1,6-dihydro-7H-pyrazolo[4,3-d]pyrimidine-7-ketone as starting materials and synthesized by multiple steps of reactions. The synthetic route is as follows:

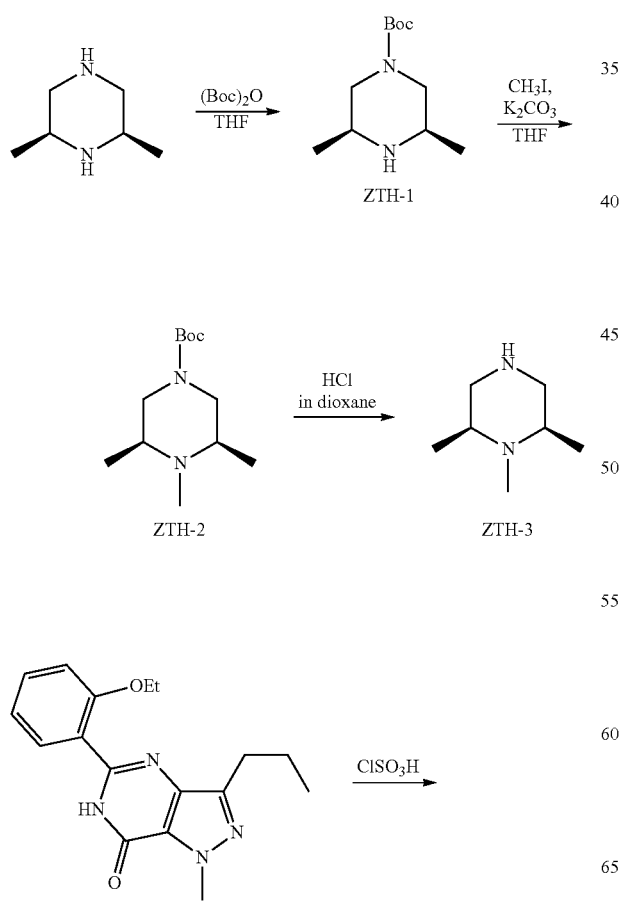

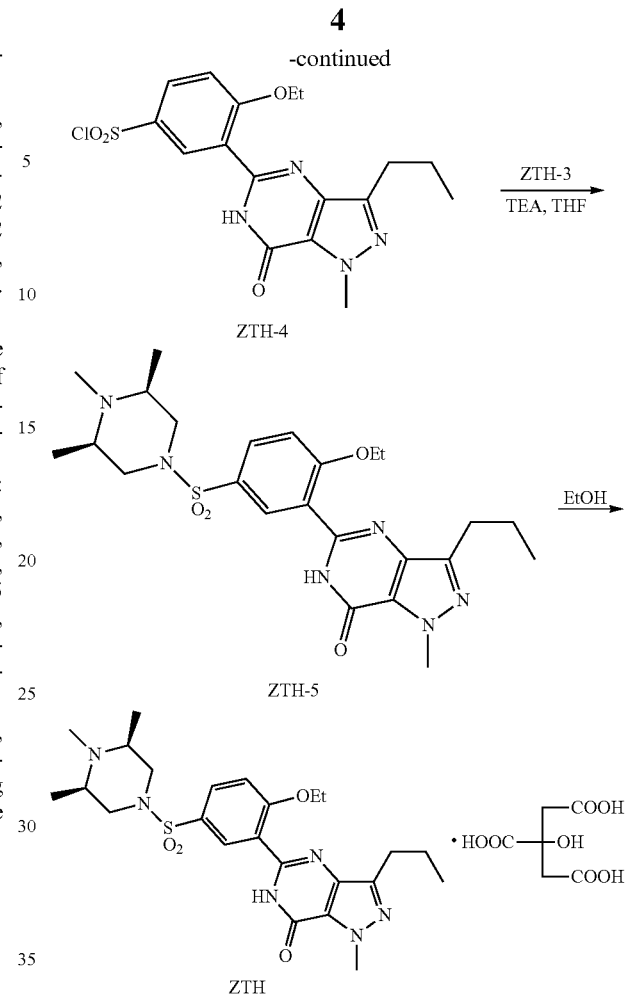

Adding tetrahydrofuran into 2,6-lupetazin and di-tert-butyl dicarbonate and reacting under room temperature, and then condensing the tetrahydrofuran to extreme, 3,5-dimethyl-1-tert-butoxycarbonyl-piperazine (ZTH-1) is obtained. Upon analyzed with nuclear magnetic resonance and mass spectrum: $^1$H-NMR (400 MHz, CDCl$_3$) δ3.8-4.1 (br, 2H), 2.75-2.80 (m, 2H), 2.2-2.5 (br, 2H), 1.45 (s, 9H), 1.052-1.067 (d, J=6 Hz, 6H). MS 215 [M+H]$^+$ Adding tetrahydrofuran, kalium carbonicum, and methyl iodide into ZTH-1 in turn, and reacting under room temperature overnight; and then filtering and condensing, adding water and dichloromethane into the residue; and rinsing with dichloromethane, merging the organic layer, rinsing with saturated brine, and drying with anhydrous sodium sulfate, condensing, and column chromatography of the residue (methanol: dichloromethane=1:20), 3,4,5-trimethyl-1-tert-butyl carbonyl piperazidine (ZTH-2) is obtained. Upon analyzed with nuclear magnetic resonance and mass spectrum: $^1$H-NMR (400 MHz, MeOD), δ4.505-4.533 (m, 2H), 4.110-4.134 (m, 2H), 2.943 (s, 3H), 2.779 (br, 2H), 2.196 (s, 9H), 1.782-1.797 (d, J=6 Hz, 6H). MS 229 [M+H]$^+$.

Dissolving ZTH-2 in dioxane, cooling, slowly adding saturated hydrochloric acid dioxane solution drop by drop, stirring under room temperature, and then evaporating the solvent under reduced pressure, 1,2,6-trimethyl piperazine (ZTH-3) is obtained. Upon analyzed with nuclear magnetic resonance and mass spectrum: $^1$H-NMR (400 MHz, MeOD) 54.505-4.533 (m, 2H), 3.722 (br, 2H), 3.611-3.644 (m, 2H), 3.310-3.423 (m, 2H), 2.937 (s, 3H), 1.493-1.506 (d, J=5.2 Hz, 6H). MS 129 [M+H]$^+$.

Dropping 5-(2-ethoxyphenyl)-1-methyl-3-propyl-1,6-dihydro-7H-pyrazolo[4,3-d]pyrimidine-7-ketone into chlorosulfonic acid, keeping reaction solution no higher than 25° C., reacting under room temperature, and then pouring the reaction solution into crushed ice, mechanically stirring under room temperature, keeping the temperature no higher than 25° C., and then filtering and drying, 5-(2-ethoxyphenyl-5-chlorosulphonyl)-1-methyl-3-propyl-1,6-dihydro-7H-pyrazolo[4,3-d]pyrimidine-7-ketone (ZTH-4) is obtained. Upon analyzed with nuclear magnetic resonance and mass spectrum: $^1$H-NMR (400 MHz, DMSO) δ 7.871-7.876 (s, 1H), 7.700-7.727 (dd, $J_1$=2 Hz, $J_2$=8.4 Hz, 1H), 7.098-7.119 (d, J=8.4 Hz, 1H), 4.125-4.161 (m, 5H), 2.778-2.816 (t, J=7.6 Hz, 2H), 1.700-1.756 (m, 2H), 1.303-1.337 (t, J=6.8 Hz, 3H), 0.919-0.956 (t, J=7.6 Hz, 3H). MS 411 $[M+H]^+$.

Adding ZTH-4, ZTH-3, and triethylamine into tetrahydrofuran, stirring under room temperature for overnight, and then evaporating solvent, adding water and methylene chloride in the residue, separating, and rinsing the methylene chloride layer with saturated sodium bicarbonate water solution, saturated brine solution in turn, and then drying and condensing, the residue obtains the compound of formula I (ZTH-5) with recrystallizing ethanol.

Adding anhydrous methanol into ZTH-5, stirring to heat up to reflow; adding citric acid after dissolved clarification; upon reflow reaction ends, cooling to room temperature, filtering, rinsing with methanol, and drying, the compound of formula II (ZTH) is obtained.

ZTH-5, ZTH-5 salts such as ZTH are pyrazolo pyrimidine ketone compounds, the chemical structures of which are similar to that of cGMP, and which can compete with cGMP to bind the catalytic domain of PDE5, so as to inhibit degradation to cGMP by PDE5, increase concentration of cGMP, to ensure that the concentration of cGMP maintains within normal range. ZTH-5, ZTH-5 salts such as ZTH can effectively inhibit activity of type 5 phosphodiesterase, and thus can be used as type 5 phosphodiesterase inhibitors or as the effective component of type 5 phosphodiesterase depressant. ZTH-5, ZTH-5 salts such as ZTH have the potential to be developed as the new generation drugs for treating erectile dysfunction, inhibiting platelet aggregation and anti-thrombosis, decreasing pulmonary hypertension and anti-cardiovascular diseases, anti-asthma and treating diabetes gastroparesis.

DETAILED DESCRIPTION OF PREFERRED EMBODIMENTS (1) Preparation of ZTH-5 (5-[2-ethoxyphenyl-5-(3,4,5-trimethyl piperazinyl)-sulfonyl]-1-methyl-3-propyl-1,6-dihydro-7H-pyrazolo[4,3-d]pyrimidine-7-ketone)

1. Preparation of 3,5-dimethyl-1-tert-butoxycarbonyl-piperazine (ZTH-1)

Adding 2,6-lupetazin (11.4 g, 100 mmol, 1 eq) and di-tert-butyl dicarbonate (21.8 g, 100 mmol, 1 eq) into a 250 ml flask; and then adding 100 ml tetrahydrofuran, reacting under room temperature for 4 hours; and condensing up tetrahydrofuran (i.e., condensing tetrahydrofuran until used up), 21.4 g orange-colored oily substance ZTH-1 is obtained, wherein the yield is 100%.

2. Preparation of 3,4,5-trimethyl-1-tert-butyl carbonyl piperazidine (ZTH-2)

Adding ZTH-1 (10.7 g, 50 mmol, 1 eq) into 250 ml flask; adding 100 ml tetrahydrofuran, kalium carbonicum (10.35 g, 75 mmol, 1.5 eq) and methyl iodide (8.52 g, 60 mmol, 1.2 eq) in turn; reacting under room temperature overnight; filtering and condensing, adding 100 ml water and 100 ml dichloromethane into the residue; and rinsing with dichloromethane (50 ml×twice), merging organic layer, rinsing with saturated brine, drying with anhydrous sodium sulfate, condensing, and column chromatography of the residue (methanol:dichloromethane=1:20), 5.7 g orange-colored oily substance ZTH-2 is obtained, wherein the yield is 50%.

3. Preparation of 1,2,6-trimethyl piperazine (ZTH-3)

Dissolving ZTH-2 (11.4 g, 50 mmol, 1 eq) in 100 ml dioxane, cooling to 0° C., and slowing adding saturated hydrochloric acid dioxane solution (4M, 25 ml, 2 eq) drop by drop, stirring under room temperature for 2 hours; and evaporating the solvent under reduced pressure, white solid crude product ZTH-3 is obtained, which is directly used for the next step without purification.

4. Preparation of 5-(2-ethoxyphenyl-5-chlorosulphonyl)-1-methyl-3-propyl-1,6-dihydro-7H-pyrazolo[4,3-d]pyrimidine-7-ketone (ZTH-4)

At a temperature of −10° C., adding 5-(2-ethoxyphenyl)-1-methyl-3-propyl-1,6-dihydro-7H-pyrazolo[4,3-d]pyrimidine-7-ketone (50 g, 160 mmo) into 100 ml chlorosulfonic acid, keeping the reaction solution at temperature no greater than 25° C. during dropping; upon dropping completes, reacting under room temperature for 3 hours; pouring the reaction liquid into crushed ice, mechanically stirring, keeping the temperature no greater than 25° C.; and then stirring under room temperature for 1 hour, filtering and drying, 50 g white solid ZTH-4 is obtained, wherein the yield is 75.9%.

5. Preparation of 5-[2-ethoxyphenyl-5-(3,4,5-trimethyl piperazinyl)-sulfonyl]-1-methyl-3-propyl-1,6-dihydro-7H-pyrazolo[4,3-d]pyrimidine-7-ketone (ZTH-5)

Add ZTH-4 (36 g, 10 mmol, 1 eq), ZTH-3 (17.6 g, 10 mmol, 1 eq), and triethylamine (60.6 g, 60 mmol, 6 eq) into 500 ml tetrahydrofuran, stirring under room temperature for overnight; evaporating the solvent; adding 200 ml water and 200 ml methylene chloride, separating, and rinsing the methylene chloride layer with saturated sodium bicarbonate water solution and saturated brine solution in turn, and then drying and condensing, the residue obtains 32 g white crystal ZTH-5 with recrystallizing 10 times amount of ethanol, and then obtains 16.5 g white crystal ZTH-5 with recrystallizing another 50 times amount of ethanol, wherein the yield is 37%.

(2) Preparation of ZTH (5-[2-ethoxyphenyl-5-(3,4,5-trimethyl piperazinyl)-sulfonyl]-1-methyl-3-propyl-1,6-dihydro-7H-pyrazolo [4,3-d]pyrimidine-7-ketone citrate)

In a 500 ml reaction vessel (bottle), adding 15 g compound ZTH-5, 270 ml anhydrous methanol, stirring to heat up to reflow; adding 12.5 g citric acid after dissolved clarification; upon reflow reaction for about 1.5 hours, cooling to room temperature, filtering, rinsing with methanol (three times×5 ml), and drying, 15 g white solid ZTH is obtained.

The above (1) and (2) are preparation embodiments, and the below (3) is an experiment embodiment.

(3) Study on inhibition effect of ZTH to PDE5

1. Inhibiting effect of ZTH to PDE5 acting on cGMP:

Experimental Method:

Enzyme-linked immune system is used to detect in-vitro inhibiting effects of ZTH with different concentration to PDE5 degrading cGMP. According to operating procedure of cGMP biotransformation enzyme-linked immunoassay system kit (ELISA kit) (also called: cGMP biotrack enzymeimmuoassy system, EIA) made by Amersham (a company), concentration of cGMP is detected. Sildenafil citrate is used as positive control.

Preparation of Reagent:

Preparation of ZTH and Sildenafil Citrate Having Different Drug Concentrations:

Weighing certain amount of ZTH to suspend in $ddh_2O$, respectively, and adding DMSO (drug:DMSO=1 mol:1 L) to have it dissolved, in the sample hole 100 ul, the final concentrations are: $10^{-4}$ mol·$L^{-1}$, $10^{-5}$ mol·$L^{-1}$, $10^{-6}$ mol·$L^{-1}$, $10^{-7}$ mol·$L^{-1}$, $10^{-8}$ mol·$L^{-1}$, $10^{-9}$ mol·$L^{-1}$, $10^{-10}$ mol·$L^{-1}$, $10^{-11}$ mol·$L^{-12}$, $10^{-12}$ mol·$L^{-1}$.

The sildenafil citrate comparator is also prepared in the same way as discussed above.

Preparation of PDE5 Working Solution:

Sucking a certain amount of PDE5, diluted with a corresponding volume of EIA buffer solution, the final concentration is 1 u/μl, which is stored under a low temperature of $-80°$ C. for later use.

Preparation of cGMP:

Weighting a certain amount of cGMP (cGMP, Na) which are dissolved in corresponding volume of EIA buffer solution, respectively, the final concentration of cGMP is 3200 fmol/50 μl, which is stored under a low temperature of $-20°$ C. for later use.

Experiment:

Degradation Effect of PDE5 to cGMP:

PDE5 and cGMP are mixed, and the sample hole 100 μl contains 3200 fmol cGMP therein, upon reacting under $30°$ C. for 20 min, to detect degradation effect of PDE5 to cGMP.

Inhibition Effect of ZTH to PDE5:

ZTH and sildenafil citrate positive control medicine are mixed with cGMP respectively and blended sufficiently (assuming use of DMSO $ddh_2O$ solution as negative control), and PDE5 3u are added and reacted under $30°$ C. for 20 min. The sample hole 100 μl contains 3200 fmol cGMP. The drug concentration can be $10^{-4}$ mol·$L^{-1}$, $10^{-5}$ mol·$L^{-1}$, $10^{-6}$ mol·$L^{-1}$, $10^{-7}$ mol·$L^{-1}$, $10^{-8}$ mol·$L^{-1}$, $10^{-9}$ mol·$L^{-1}$, $10^{-10}$ mol·$L^{-1}$, $10^{-11}$ mol·$L^{-1}$, $10^{-12}$ mol·$L^{-1}$, to detect inhibition of different concentration of ZTH, positive control medicine to PDE5 degrading on cGMP. The above test samples are added into test holes coated by antibody, and then 100 ul antiserum are added respectively to suspend reaction, which are effected under $4°$ C. for 15-18 h, and then adding cGMP peroxidase conjugate 50 μl to suspend reaction, effected for 3 h and then washed, adding TMB 200 μl for color development, and BIORAD 450 ELISA reader is used to read at a wavelength of 630 nm. Based on the measured cGMP absorbance value, % B/BO is calculated using EIA absorbance formula [(standard or sample OD-NSB OD)×100/(0 standard OD-NSB OD)]. With linear regression to fit S curve and PROBIT regression function, IC 50 of ZTH, sildenafil citrate positive control medicine to PDE5 is calculated.

Results of the Experiment:

Degradation of PDE5 to cGMP:

PDE5 reacts with cGMP under $30°$ C. for 20 min, and then PDE5 can degrade 3200 fmol cGMP to about 1600 fmol.

Inhibition effect of ZTH to PDE5 degrading on cGMP:

Inhibition effect of different concentration ($10^{-4}$ mol·$L^{-1}$, $10^{-5}$ mol·$L^{-1}$, $10^{-6}$ mol·$L^{-1}$, $10^{-7}$ mol·$L^{-1}$, $10^{-8}$ mol·$L^{-1}$, $10^{-9}$ mol·$L^{-1}$, $10^{-10}$ mol·$L^{-1}$, $10^{-11}$ mol·$L^{-1}$, $10^{-12}$ mol·$L^{-1}$) of ZTH, control medicine and DMSO $ddH_2O$ solution groups to PDE5 degrading on cGMP are compared, respectively. Based on different absorbance (OD value) obtained from different concentration of ZTH inhibiting PDE5 to degrade on cGMP, using EIA absorbance formula to calculate % B/BO[(standard or sample OD-NSB OD)×100/(0 standard OD-NSB OD)], IC50 value of the drug is calculated. With linear regression fitting, data can be fitted to S curve ($p<0.05$); with PROBIT regression function, IC50 is calculated. IC50 value of ZTH is $2.12\times10^{-9}$M, and sildenafil citrate positive control medicine is $6.958\times10^{-9}$M.

2. Effect of ZTH to PDE 5 on cAMP:

Experimental Method:

Enzyme-linked immune system is used to detect in-vitro effects of ZTH with different concentration to PDE5 on cAMP. According to operating procedure of cAMP biotransformation enzyme-linked immunoassay system kit (ELISA kit) (also called: cAMP biotrack enzymeimmuoassy system, EIA) made by Amersham, concentration of cAMP is detected. Sildenafil citrate is used as a control.

Preparation of Reagent:

Preparation of cAMP:

A certain amount of cAMP (cAMP, Na) is weighted, and dissolved in corresponding volume of EIA buffer solution, respectively. The final concentration of cAMP is 1600 fmol/50 μl. The product is stored under a low temperature of $-20°$ C. for later use.

Preparation of ZTH and sildenafil citrate, and preparation of PDE5 working solution are same as discussed above.

Experiment:

Degradation Effect of PDE5 to cAMP:

PDE5 and cAMP are mixed, and sample hole 100 μl contains 1600 fmol cAMP. Upon reacted under $30°$ C. for 20 min, degradation effect of PDE5 to cAMP is detected.

Effect of ZTH to PDE5 on cAMP:

ZTH and positive control medicine are mixed with cAMP and blended sufficiently (assuming use of DMSO $ddh_2O$ solution as negative control), and PDE5 3u are added and reacted under $30°$ C. for 20 min. The sample hole 100 μl contains 1600 fmol cAMP. The drug concentration can be $10^{-4}$ mol·$L^{-1}$, $10^{-5}$ mol·$L^{-1}$, $10^{-6}$ mol·$L^{-1}$, $10^{-7}$ mol·$L^{-1}$, $10^{-8}$ mol·$L^{-1}$, $10^{-9}$ mol·$L^{-1}$, $10^{-10}$ mol·$L^{-1}$, $10^{-11}$ mol·$L^{-1}$, $10^{-12}$ mol·$L^{-1}$. The above test samples are added into test holes coated by antibody, and then 100 ul antiserum are added respectively to suspend reaction, which are effected under $4°$ C. for 2 h, and then adding cAMP peroxidase conjugate 500 to suspend reaction, effected for 1 h and then washed, adding TMB 150 μl for color development, and ELISA reader is used to read at a wavelength of 630 nm. Based on the measured cAMP absorbance value, % B/BO is calculated using EIA absorbance formula [(standard or sample OD-NSB OD)×100/(0 standard OD-NSB OD)]. With linear regression to fit S curve and PROBIT regression function, IC 50 of ZTH, sildenafil citrate positive control medicine to PDE5 is calculated.

Results of the Experiment:

Degradation effect of PDE5 to cAMP:

PDE5 does not degrade cAMP.

Effect of ZTH to PDE5 on cAMP:

There is no substantial difference in OD value among ZTH group, control medicine group, and ddH$_2$O medicine negative control group (p>0.05), and S curve cannot be fitted (p>0.05).

CONCLUSION

ZTH is pyrazolo pyrimidine ketone compound, the chemical structure of which is similar to that of cGMP, and which can compete with cGMP to bind the catalytic domain of PDE5, so as to inhibit PDE5 to degrade on cGMP, and increase concentration of cGMP Upon studying inhabitation effect of ZTH to PDE5 degrading on cGMP, IC50 of ZTH is calculated as $2.12\times10^{-9}$M, and the positive control medicine is $6.958\times10^{-9}$M. The result indicates that ZTH can inhibit PDE5 to degrade cGMP and have dependency on dosage, and is a very good PDE5 inhibitor. Its inhibiting activity of PDE5 enzyme is significantly better than sildenafil citrate. Thus, it has a potential to be a new generation drug for treating erectile dysfunction, inhibiting platelet aggregation and anti-thrombosis, decreasing pulmonary hypertension and anti-cardiovascular diseases, anti-asthma and treating diabetes gastroparesis.

In the above experimental embodiments, even though only the experimental data of ZTH is disclosed, in view that ZTH is citrate of ZTH-5 and ZTH-5 has similar structure to ZTH (i.e., ZTH-5 and salts of ZTH-5 other than citrate have similar structure to ZTH, and have common pyrazolo pyrimidine ketone structure), it can be deduced from the experimental effects of ZTH that ZTH-5, salts of ZTH-5 other than citrate have the effects of inhibiting PDE5 to degrade cGMP to become PDE5 inhibitor, and have potential to be a new generation drug for treating erectile dysfunction, inhibiting platelet aggregation and anti-thrombosis, decreasing pulmonary hypertension and anti-cardiovascular diseases, anti-asthma and treating diabetes gastroparesis.

We claim:

1. A compound 5-1-methyl-3-propyl-1,6-dihydro-7H-pyrazolo pyrimidine-7-ketone citrate as represented by formula II:

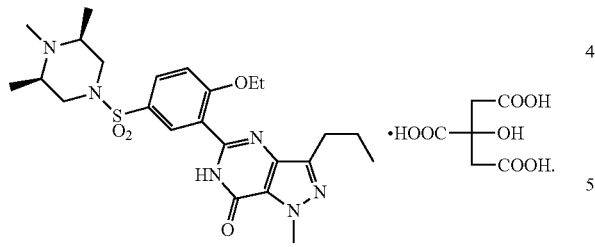

(II)

2. A pharmaceutical composition comprising an effective amount of 5-1-methyl-3-propyl-1,6-dihydro-7H-pyrazolo pyrimidine-7-ketone citrate according to claim 1, and a carrier and/or excipient.

3. A method of preparing a compound, the method comprising the following steps:
   (1) combining tetrahydrofuran and 2,6-lupetazin and di-tert-butyl dicarbonate, reacting at room temperature, and condensing the tetrahydrofuran to obtain 3,5-dimethyl-1-tert-butoxycarbonyl-piperazine;
   (2) adding tetrahydrofuran, kalium carbonicum, and methyl iodide to 3,5-dimethyl-1-tert-butoxycarbonyl-piperazine obtained in step (1), reacting at room temperature overnight, and then filtering and condensing to obtain a residue, adding water and dichloromethane to the residue, and extracting with dichloromethane to obtain an organic layer, merging the organic layer, rinsing with saturated brine, drying with anhydrous sodium sulfate, condensing to obtain a residue, and column chromatography of the residue with a solution of methanol and dichloromethane at a ratio of 1:20, to obtain 3,4,5-trimethyl-1-tert-butyl carbonyl piperazidine;
   (3) dissolving 3,4,5-trimethyl-1-tert-butyl carbonyl piperazidine obtained in step (2) in dioxane as a solvent, cooling, and slowly adding saturated hydrochloric acid dioxane solution drop by drop, stirring at room temperature, and then evaporating the dioxane solvent under reduced pressure to obtain 1,2,6-trimethyl piperazine;
   (4) dropping 5-(2-ethoxyphenyl)-1-methyl-3-propyl-1,6-dihydro-7H-pyrazolo pyrimidine-7-ketone into chlorosulfonic acid to form a reaction solution, maintaining the reaction solution at a temperature no higher than 25° C., and then pouring the reaction solution into crushed ice, mechanically stirring at a temperature no higher than 25° C., and then filtering and drying to obtain 5-(2-ethoxyphenyl-5-chlorosulphonyl)-1-methyl-3-propyl-1,6-dihydro-7H-pyrazolo pyrimidine-7-ketone; and
   (5) combining 5-(2-ethoxyphenyl)-1-methyl-3-propyl-1,6-dihydro-7H-pyrazolo pyrimidine-7-ketone obtained in step (4) and 1,2,6-trimethyl piperazine obtained in step (3), and triethylamine with tetrahydrofuran as a solvent, stirring at room temperature overnight, and then evaporating the solvent to obtain a residue, adding water and methylene chloride to the residue, separating, extracting the methylene chloride layer with a saturated sodium bicarbonate water solution and a saturated brine solution, and then drying and condensing to obtain the compound of formula I with recrystallization of ethanol; wherein formula I is

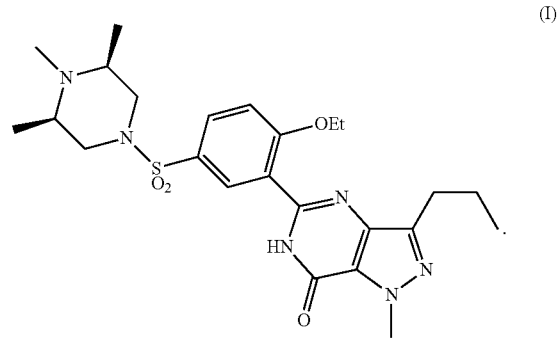 [SMILES: CCCc1nn(C)c2c(=O)[nH]c(-c3cc(S(=O)(=O)N4C[C@@H](C)N(C)[C@@H](C)C4)ccc3OCC)nc12]

(I)

in which chemical name of the compound represented by formula I is: 5-1-methyl-3-propyl-1,6-dihydro-7H-pyrazolo pyrimidine-7-ketone.

4. A method of preparing the compound of claim 1, the method comprising:
   adding anhydrous methanol to the compound of Formula I to form a solution, stirring the solution to heat up to reflow, adding citric acid to the solution after clarification, upon reflow reaction, cooling to room temperature, filtering, rinsing with methanol, and drying to obtain the compound of claim 1.

* * * * *